United States Patent [19]
Matsuura et al.

[11] Patent Number: 5,716,353
[45] Date of Patent: Feb. 10, 1998

[54] CRYOSURGICAL INSTRUMENT

[75] Inventors: David G. Matsuura, Escondido; Paul F. Zupkas, San Diego, both of Calif.

[73] Assignee: URDS, Corp., San Diego, Calif.

[21] Appl. No.: 642,658

[22] Filed: May 3, 1996

[51] Int. Cl.$^6$ ............................................. A61B 17/38
[52] U.S. Cl. ................................................ 606/22; 606/20
[58] Field of Search ..................... 606/20–26; 607/96, 607/105

[56] References Cited

U.S. PATENT DOCUMENTS

| | | | |
|---|---|---|---|
| 4,946,460 | 8/1990 | Merry et al. | 606/21 |
| 5,520,682 | 5/1996 | Baust et al. | 606/24 |
| 5,573,532 | 11/1996 | Chang et al. | 606/26 |
| 5,624,392 | 4/1997 | Saab | 606/21 |

*Primary Examiner*—Jennifer Bahr
*Assistant Examiner*—David M. Ruddy
*Attorney, Agent, or Firm*—Donald E. Stout

[57] ABSTRACT

A cryosurgical instrument incorporates a heat transfer zone, which abuts against the portion of the cryosurgical instrument near the input refrigerant entrance, and which receives pure input refrigerant at the coldest temperature for quickly and effectively cooling this portion of the cryosurgical instrument. The cryosurgical instrument includes a shaft portion and a handle portion. The shaft portion includes an outer jacket tube having both an open and closed end. The closed end surrounds the freezing zone for freezing live tissue. A middle tube is disposed within the outer jacket tube. An inner tube is disposed within the middle tube. The inner tube is adapted for routing input cryogenic refrigerant therethrough to the freezing zone. The channel between the inner tube and middle tube forms a cryogenic refrigerant exhaust path for exhausting cryogenic refrigerant from the freezing zone. A heat transfer zone is disposed within the handle portion of the cryosurgical instrument near the entrance of the input refrigerant. The heat transfer zone may take the form of a cooling chamber. The cooling chamber is in fluid communication with the inner tube to receive input cryogenic refrigerant from inlet ports therefrom, and is adapted for circulating input refrigerant within the cooling chamber to induce heat transfer from the walls of the chamber into the refrigerant. The cryosurgical instrument further includes an exhaust chamber disposed within the handle portion adapted for receiving exhaust cryogenic refrigerant from the exhaust path. The exhaust chamber is also adapted for receiving exhaust cryogenic refrigerant from the cooling chamber through outlet ports in the cooling chamber.

20 Claims, 2 Drawing Sheets

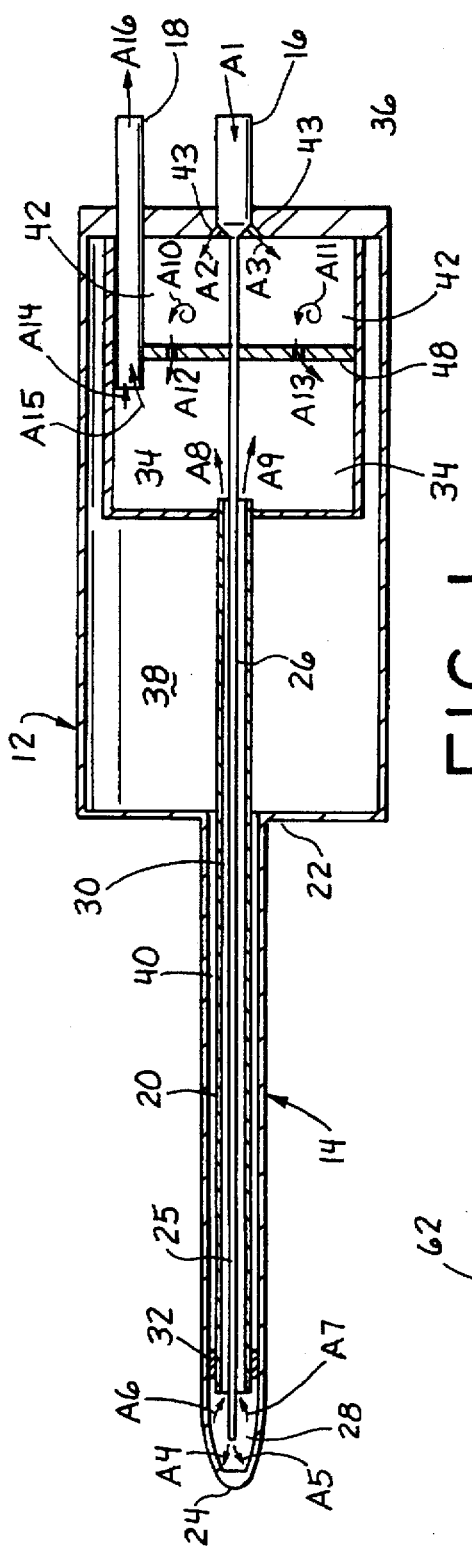
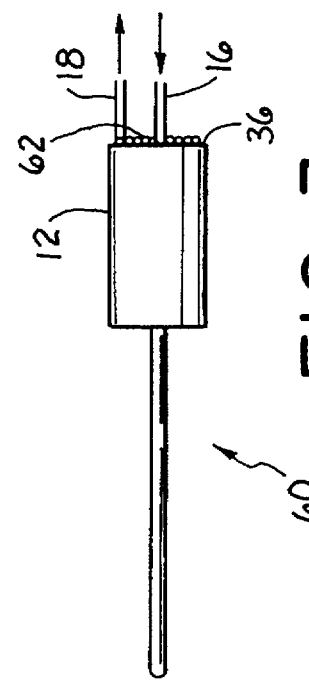
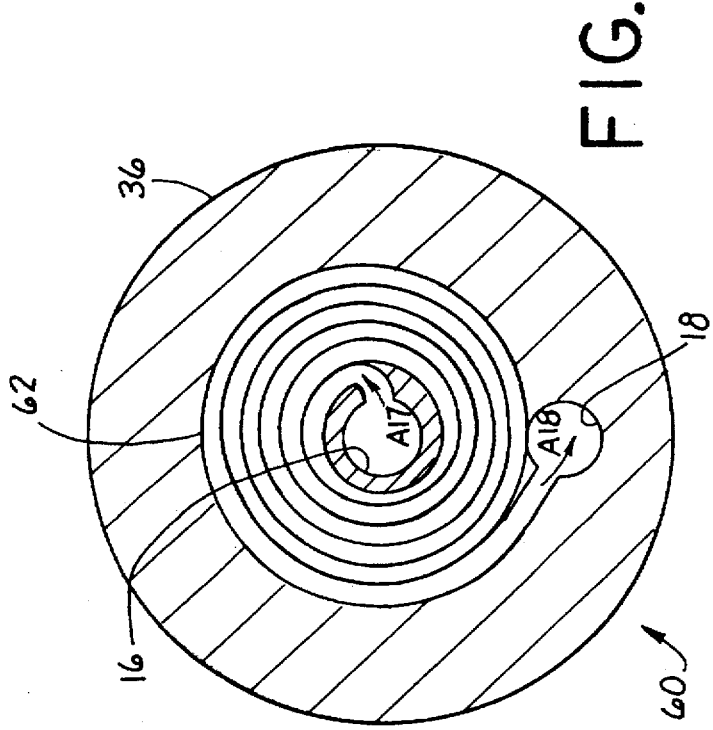
FIG. 1
FIG. 3
FIG. 4

CRYOSURGICAL INSTRUMENT

BACKGROUND OF THE INVENTION

1. Field of the Invention

The present invention relates generally to a cryosurgical instrument suitable for use in performing cryoablation of body tissue and, more particularly, to a surgical cryoprobe instrument capable of rapidly producing and maintaining very low temperatures.

2. Description of Related Arts

Cryosurgical instruments are used to destroy or cryoablate tissue by freezing. Modern cryosurgical procedures are used in opthalmology, dermatology, gynecology, and other fields of medicine. Cryoprobes are cryosurgical instruments, which use liquefied gases, such as nitrogen or oxygen, or which rely upon the adiabatic expansion of gases to cause freezing of tissue at the tip of the cryoprobe shaft. The remainder of the cryoprobe shaft, which is also in contact with tissue, is insulated. The tip of the cryoprobe is effective for freezing diseased tissue beneath the surface of the skin, without physically exposing the diseased tissue or damaging healthy tissue between the diseased tissue and the skin surface. The tip of the cryoprobe contacting the diseased area of tissue removes thermal energy, resulting in tissue destruction of cryoablation.

A typical cryoprobe includes a handle portion and a shaft portion. A commonly used shaft portion design incorporates three concentric tubes. The outer tube forms the external surface of the shaft portion. The inner tube forms the refrigerant inlet path for supplying refrigerant to a freezing chamber at distal end of the shaft portion. A channel between the inner tube and the middle tube forms the refrigerant outlet path, where refrigerant is removed from the distal end of the shaft portion.

The channel between the middle tube and the outer tube is sealed at the distal end to create a freezing chamber at the tip that allows communication between the middle and inner tubes. Sealing the channel between the middle and outer tubes prevents ingress of refrigerant into the proximal portion of this channel. The channel between the middle and outer tubes from the proximal end to the distal seal forms an insulating barrier between the outlet path of the refrigerant and the surface of the outer shaft, which contacts the tissue. The insulating barrier prevents tissue contacting the outer shaft from freezing. The insulation barrier may employ active or passive means to prevent the transfer of thermal energy between the outlet refrigerant path and the surface of the outer shaft.

The handle portion of the cryoprobe includes two outside connectors for supplying and removing refrigerant from the cryoprobe. The two outside connectors communicate with spaces in the handle portion that direct the path of the refrigerant into and out of the shaft portion. The handle also serves as a point of manipulation for the operator.

Cryoprobes are typically made of metal to promote the transfer of thermal energy and to provide the strength required to withstand both high pressure, which can be on the order of 2000 pounds per square inch (psi), and thermalstresses due to large temperature variations, which can exceed 400 degrees Fahrenheit. The most effective transfer of thermal energy and therefore destruction of tissues occurs when the tip of the cryoprobe shaft portion is maintained at the lowest possible temperature. A number of factors affect the attainable temperature of this tip, including the design of the cryoprobe, the flow of refrigerant, and the temperature of the refrigerant. Thermal energy transfer at the tip is optimized when the least amount of heat is introduced into the refrigerant, before the refrigerant reaches the tip. Any undesirable leakage of heat into the refrigerant prior to reaching the tip of the cryoprobe, reduces the transfer thermal energy at the tip and thus its capacity to destroy tissue.

U.S. Pat. No. 5,254,116, which issued to Baust et at., discloses a cryosurgical instrument for attenuating thermal energy leakage into the input refrigerant, before the input refrigerant is routed to the tip of the cryosurgical instrument. The cryosurgical instrument includes a handle portion and a shaft portion. As shown in FIG. 1 of this patent, an inlet 21 routes refrigerant through a large diameter portion 25 and a small diameter portion 28 of a supply tube 22. The refrigerant expands into the distally located freeze zone 15, and is then routed out of the cryosurgical instrument through the exhaust flow channel 24 and the exhaust 50. Vent holes 29, 29a, and 29b are disposed along the supply tube 22.

The vent holes maintain a high flow rate of the refrigerant from the inlet 21 to the probe tip 20, by venting any gases present or formed in the supply tube into the exhaust tube before the gas can impede the flee flow of refrigerant through the supply tube. A second function of the vent holes is to vent gas along the supply tube 25, which may be formed by heat exchange between the counter-current flow of the exhaust refrigerant and the input refrigerant. A third function of the vent holes is to decrease the extent of the counter-current heat exchange by venting some of the refrigerant drops through the vent holes into the returning path of the exhaust refrigerant, thereby slightly cooling the exhaust refrigerant When the prior art cryosurgical instrument is initially activated, refrigerant passing through the inlet 21 is in contact with the proximal handle portion 40 at a temperature as much as 220 degrees Celsius warmer than that of the handle portion 40. Thermal energy transfer from this proximal handle portion 40 into the refrigerant reduces the energy transfer capacity of the refrigerant at the tip 20 of the cryosurgical instrument. Although this proximal handle portion 40 is eventually cooled by the refrigerant passing through the inlet 21, the equilibrium established includes the flow of thermal energy from the environment through the proximal handle portion 40 into the refrigerant at a gradient of 220 degrees Celsius. It is desirable to cool the tip 20 as fast as possible, but cooling of this tip 20 is limited by the initial cooling of the proximal handle portion and the equilibrium flow of heat into the refrigerant through the proximal handle portion 40. Although the vent holes disclosed in the '116 patent operate to cool the exhaust refrigerant slightly, a device is still needed to more quickly and efficiently cool the proximal handle portion of the cryosurgical instrument.

SUMMARY OF THE INVENTION

The cryosurgical instrument of the present invention incorporates a heat transfer zone, which abuts against the proximal end of the cryosurgical instrument, and which receives pure input refrigerant at the coldest practicable temperature for quickly and effectively cooling the proximal end of the cryosurgical instrument and reducing the equilibrium flow of heat into the refrigerant. The cryosurgical instrument of the present invention includes a handle portion and a shaft portion, the shaft portion having a distal closed end and an open proximal end, The closed end of the outer tube surrounds a freezing zone for freezing live tissue. The shaft portion is constructed of three concentric tubes, comprising an inner, middle, and an outer tube. The outer tube forms the outer jacket or surface of the shaft portion. The middle tube is disposed within the outer tube. The inner tube is disposed within the middle tube. Channels are created between the middle and outer tubes and the inner and middle tubes. The inner tube is adapted for routing input cryogenic refrigerant to the freezing zone at the distal closed end of the shaft portion. The channel between the middle and inner tubes forms a cryogenic refrigerant exhaust path for exhausting cryogenic refrigerant from the freezing zone. The freeze zone is defined at the tip of the shaft portion by a barrier or spacer in the channel between the outer and middle tubes and the distal closed end of the outer tube, thereby creating a unique circulating path for refrigerant in the freeze zone. The barrier or spacer further defines a proximal portion of the channel between the middle and outer tubes that is sealed to the ingress of refrigerant from the freeze zone. The proximal portion of the channel between the middle tube and the outer tube is insulated using an insulating material, a vacuum, a heat regulating system, or other methods that control the transfer of thermal energy between the middle and outer tubes.

The cryosurgical instrument further includes a cryoprobe handle portion, which includes a proximal side and a distal side. In one embodiment of the present invention, the heat transfer zone comprises a cooling chamber which is disposed at the proximal end of the handle portion of the cryosurgical instrument. The cooling chamber is in fluid communication with the inner tube to receive input cryogenic refrigerant through one or more refrigerant inlet ports. The cooling chamber is adapted for routing the input cryogenic refrigerant from the inlet ports, through the cooling chamber, and to the cryogenic refrigerant exhaust path through one or more outlet ports. The cooling chamber inlet and outlet ports are positioned to maximize circulation of refrigerant within the cooling chamber and the transfer of thermal energy from the walls of the cooling chamber into the refrigerant. The cryosurgical instrument further includes an exhaust chamber, which is adapted for receiving exhaust cryogenic refrigerant from the cryogenic exhaust path. The exhaust chamber is also adapted for receiving exhaust cryogenic refrigerant from the cooling chamber.

An insulating chamber is disposed in the handle portion in contact with the wall forming the outer jacket or surface of the handle portion. This insulating chamber communicates with the insulated proximal shaft portion and surrounds portions of the exhaust chamber and the cooling chamber. The proximal side of the cryoprobe handle portion forms a proximal side of the cooling chamber, and the inner tube passes through an aperture in this proximal side of the cryoprobe handle portion. Although the insulation chamber surrounds most of the exhaust chamber and the cooling chamber, the insulation chamber does not surround the proximal side of the cooling chamber. Since this proximal side of the cooling chamber is not surrounded by the insulation chamber, it is not insulated as well from the external environment. Consequently, input refrigerant passing through the inner tube, which passes through an aperture in the proximal side of the cryoprobe handle portion, is subject to thermal leakage. The cooling chamber of the present invention is adapted for attenuating this thermal leakage by cooling the proximal side of the cryoprobe handle with pure input refrigerant, to thereby prevent heat from leading into the inner tube at the proximal side of the cryoprobe handle portion.

According to another embodiment of the present invention, the heat transfer zone comprises a heat exchanger which is disposed near the proximal side of the cryoprobe handle portion, to thereby maintain this proximal side at a very low temperature. The heat exchanger includes a tube, which is fed with input cryogenic refrigerant to thereby quickly cool the proximal side of the cryoprobe handle portion to a very low temperature and maintain this very low temperature. The tube of the heat exchanger may be coiled and placed in contact with the proximal side of the cryoprobe handle portion.

The present invention, together with additional features and advantages thereof, may best be understood by reference to the following description taken in connection with the accompanying illustrative drawings.

BRIEF DESCRIPTION OF THE FIGURES

FIG. 1 is cross-sectional view of the cryosurgical instrument according to a first preferred embodiment of the present invention;

FIG. 3 is a first side elevational view of the cryosurgical instrument according to a second embodiment of the present invention; and FIG. 4 is a second side elevation view of the cryosurgical instrument according to the second embodiment of the present invention.

DETAILED DESCRIPTION OF THE PREFERRED EMBODIMENTS

Figure 2:
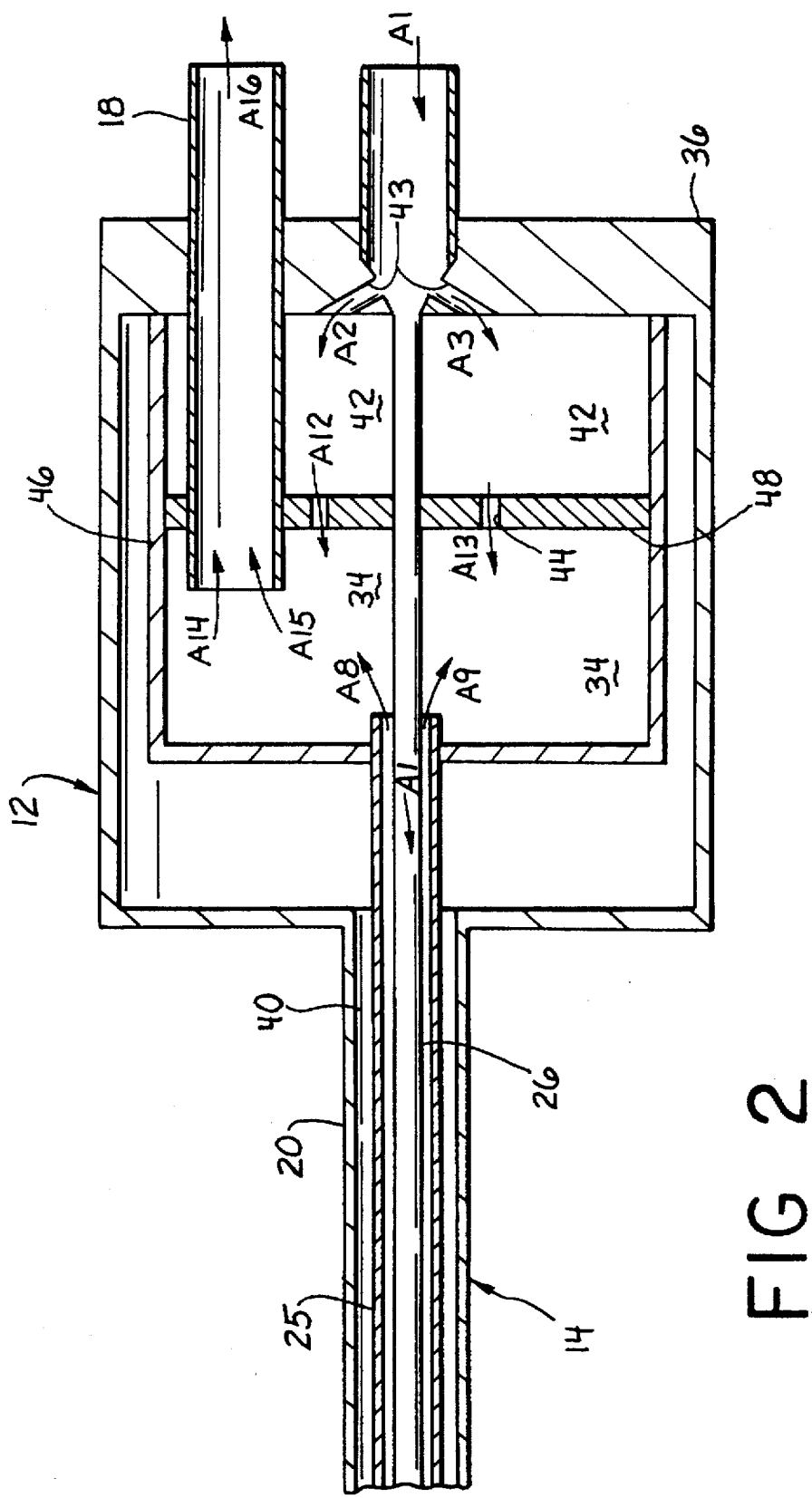
FIG. 2 is an enlarged cross-sectional view of the cryosurgical instrument of the first preferred embodiment off the present invention.

Turning to FIG. 1, a cryosurgical instrument 10 is illustrated, having a cryoprobe handle portion 12 and a cryoprobe shaft portion 14. The cryoprobe handle portion 12 comprises a supply tube inlet connection 16 for supplying input cryogenic refrigerant to the cryosurgical instrument 10 and an exhaust tube connection 18 for removing exhaust cryogenic refrigerant from the cryosurgical instrument 10.

The cryoprobe shaft portion 14 comprises an outer jacket tube 20, which includes an open proximal end 22 and a closed distal tip 24. In the presently preferred embodiment, the cryogenic refrigerant comprises liquid nitrogen, and the cryosurgical instrument comprises metal. The distal tip 24 of the cryosurgical instrument 10 may comprise any metal and, more particularly, may comprise stainless steel. The open proximal end 22 of the outer jacket tube 20 is connected to the cryoprobe handle portion 12. A middle exhaust tube 25 is disposed within the outer jacket tube 20, and an inner supply tube 26 is disposed within the middle exhaust tube 25. In the presently preferred embodiment, the outer jacket tube 20, the middle exhaust tube 25, and the inner supply tube 26 are all concentric, but other configurations are possible.

Input cryogenic refrigerant is routed under pressure through the inner supply tube 26 to a sealed expansion chamber 28, which is disposed near the distal tip 24 of the cryosurgical instrument 10. A channel between the inner supply tube 26 and the middle tube 25 forms a cryogenic refrigerant exhaust path 30. Input cryogenic refrigerant exiting from the inner supply tube 26 into the sealed expansion chamber 28 draws thermal energy from the distal tip 24 of the cryosurgical instrument, to thereby maintain the distal tip 24 at a very low temperature.

As cryogenic refrigerant exits the inner supply tube 26 and expands into the expansion chamber 28, thermal energy is transferee from the tissue in contact with the distal tip 24 of the cryosurgical instrument 10 into the cryogenic refrigerant. The temperature of the cryogenic refrigerant within the sealed expansion chamber 28 rises, and may form vapors. The formation of vapor reduces the efficiency of the heat transfer between the input refrigerant and the tissue surrounding the distal tip 24. The formation of vapor within the expanded refrigerant requires the exhaust path 30 to be of sufficient cross-sectional area to allow the rapid removal of expanded refrigerant from the expansion chamber 28.

Expanded or exhaust cryogenic refrigerant passes through the exhaust path 30 in the shaft portion 14 created by the channel between the inner supply tube 26 and middle exhaust tube 25. The exhaust path 30 is in communication with an exhaust chamber 34 in the handle portion 12 of the cryosurgical instrument 10. The exhaust refrigerant flows from the exhaust path 30 into the exhaust chamber 34 and, subsequently, exits the cryosurgical instrument 10 through the exhaust tube connection 18.

An annular barrier or spacer 32 prevents the expanded cryogenic refrigerant from entering into an area between the outer jacket 20 and the middle exhaust tube 25. The distal tip 24 of the cryosurgical instrument 10 is maintained at a very low temperature, but the remainder of the outer jacket of the cryoprobe shaft portion 14 is preferably insulated to prevent damage to tissue contacting areas of the cryoprobe shaft portion 14 other than the distal tip 24. The outer surface of cryoprobe handle portion 12 is also preferable insulated to avoid damage to the operator during manipulation of the cryosurgical instrument 10 and prevent thermal leakage from the external environment into the refrigerant paths.

However, the rear potion 36 of this cryoprobe handle portion 12 is left in contact with both the external environment and the supply tube inlet connection 16. Without taking into account the improvements of the present invention, when the cryogenic refrigerant initially passes through the supply tube inlet connection 16, it would tend to receive thermal energy from the rear portion 36 of the cryoprobe handle 12. Due to the large temperature differential between the inlet refrigerant and the rear portion 36 of the handle 12, significant thermal energy would leak into the refrigerant, thereby raising its temperature and reducing its ability to quickly and efficiently cool the distal tip 24 of the cryosurgical instrument 10. Once the rear portion 36 of the cryoprobe handle 12 is adequately cooled by the cryogenic refrigerant passing through the supply tube inlet connection 16, more effective cooling of the distal tip 24 can occur. Thermal energy will continue to seep into the cryogenic refrigerant as the cryogenic refrigerant passes through the supply tube inlet connection 16, however, unless the rear portion 36 of the cryoprobe handle 12 is maintained at a temperature substantially equal to the temperature of the cryogenic refrigerant passing through the supply tube inlet connection 16.

The insulation of the outer surface of the cryoprobe handle portion 12 from the internal refrigerant paths is accomplished by an insulation chamber 38 disposed within the cryoprobe handle portion 12. In a preferred embodiment, insulation is accomplished is by creating a vacuum in the insulation chamber 38. The vacuum insulation chamber 38 is in fluid communication with the insulating channel 40, located between the outer jacket tube 20 and the middle exhaust tube 25 at the proximal portion of the shaft portion 14. In the presently preferred embodiment, the vacuum insulation chamber 38 comprises a vacuum, but other insulating materials or methods may be used in the insulation chamber 38 and the insulating channel 40 to provide insulation. Additionally, insulating tape may be wrapped around the cryoprobe handle portion 12 and or the cryoprobe shaft portion 14.

In one preferred embodiment, the vacuum insulation chamber 38 extends partially around the exhaust chamber 34, and further extends around a rear cooling chamber 42. As best seen in FIG. 2, the rear cooling chamber 42 receives input cryogenic refrigerant from the supply tube inlet connection 16 and thereby functions to rapidly cool the rear portion 36 of the cryoprobe handle 12 to approximately the same temperature as the input cryogenic refrigerant. The cryogenic refrigerant enters into the rear cooling chamber 42 through refrigerant inlet ports 43. The rear cooling chamber 42 of the present invention operates to cool the rear portion of the cryoprobe handle 36 very quickly, by circulating refrigerant at its lowest temperature within the cooling chamber 42. Thermal energy is transferred from the rear portion of the cryoprobe handle 36 into the refrigerant circulating in the cooling chamber 42, thereby reducing the leakage of thermal energy from the rear portion of the cryoprobe handle 36 into the refrigerant as it enters the supply tube inlet connection 16. Cryogenic refrigerant circulating within the rear cooling chamber 42 exits through outlet ports 44 into the exhaust chamber 34.

Inlet ports 43 and outlet ports 44 are positioned to promote the circulation of refrigerant in the rear cooling chamber and maximize the thermal energy transfer between the refrigerant and the rear portion of the cryoprobe handle 36. The positions of the inlet ports 43 and outlet ports 44 are dependent upon the shape of the chamber and the number of ports. In a preferred embodiment the chamber is cylindrical in shape and possesses two outlet ports 44 and two inlet ports 43. The inlet ports are located in the proximal portion of the inner supply tube 26 as it passes through the center of the cooling chamber 42. The inlet ports 43 are located on opposite sides of the inner supply tube 26, 180° from one another. The outlet ports 44 are located at the outer radius in the distal chamber wall 48. The outlet ports 44 are located on opposite sides of the distal chamber wall 48, 180° from one another. The outlet ports 44 are in turn offset from the inlet ports 43. Optimizing the positioning of the inlet ports 43 and outlet ports 44 in this manner promotes the circulation of refrigerant within the cooling chamber 42 and maximizes the heat exchange between the refrigerant and the cooling chamber walls.

The exhaust cryogenic refrigerant from the rear cooling chamber 42 is combined with exhaust cryogenic refrigerant from the distal tip 24 in the exhaust chamber 34. The combined exhaust refrigerant is routed out of the cryosurgical instrument 10 through the exhaust tube connection 18. A chamber wall 46 surrounds both the exhaust chamber 34 and the rear cooling chamber 42 and defines the inner surface of the insulating chamber 38.

A common wall 48 divides the exhaust chamber 34 from the rear cooling chamber 42. According to the present invention, the rear cooling chamber 42 is separate and distinct from the exhaust chamber 34. Since the exhaust cryogenic refrigerant from the distal tip 24 is typically warmer than the input cryogenic refrigerant passing through the supply tube inlet connection 16, an important feature of the present invention involves filling the rear cooling chamber 42 with only input cryogenic refrigerant. This is assured because the pressure in the cooling chamber 42 is maintained substantially at the pressure of the supply tube inlet 16, which is higher than the pressure in the exhaust chamber 34. The filling of the rear cooling chamber 42 with input cryogenic refrigerant exclusively from the supply tube inlet connection 16 achieves a minimum cooling of the rear portion of the cryoprobe handle 36.

In operation, input cryogenic refrigerant enters through the supply tube inlet connection 16 in the direction of the arrow A1, and a portion of the input cryogenic refrigerant is routed into the rear cooling chamber 42 through the refrigerant inlet ports 43. This input cryogenic refrigerant passes through the refrigerant inlet ports 43 in the directions of the arrows A2 and A3, and circulates within the rear cooling chamber 42 in the directions of the arrows A10 and A11 (FIG. 1). The cryogenic refrigerant exits through the rear cooling chamber 42 through the outlet ports 44 in the directions of the arrows A12 and A13 (FIG. 2). Input cryogenic refrigerant within the inner supply robe 26 exits into the sealed expansion chamber 28 in the directions of the arrows A4 and A5 (FIG. 1) and cools the distal tip 24 of the cryosurgical instrument 10. The exhaust cryogenic refrigerant is routed into the cryogenic refrigerant exhaust path 30, in indicated by the arrows A6 and A7. This exhaust cryogenic refrigerant travels in the directions of the arrows A8 and A9 (FIG. 2) to exit from the cryogenic refrigerant exhaust path 30 into the exhaust chamber 34. The cryogenic refrigerant from the cryogenic refrigerant exhaust path 30 and from the rear cooling chamber 42 combine and enter into the exhaust tube connection 18, as indicated by the arrows A14 and A15. The cryogenic refrigerant exits from the exhaust tube connection 18 in the direction of the arrow A16.

The difference in temperatures between refrigerant in the supply and exhaust paths is high at the onset of flow and decreases dramatically as flow in the cryosurgical instrument 10 continues with time until the difference reaches as little as 5 to 10 degrees Celsius (typically in 2–3 minutes). This difference is very small compared to the difference between the rear of the handle 36 (at room temperature of approximately 25 degrees Celsius) and the inlet supply tube connection 16 (at a cryogenic refrigerant temperature of approximately minus 190 degrees Celsius). The rear portion 36 of the handle 12 contacts the outside at room temperature, and also contacts the supply tube inlet connection 16, thereby creating a heat transfer path from the outside environment to the cryogenic refrigerant.

The need for strength in the cryoprobe handle portion 12 requires the cryoprobe handle portion 12 to be constructed of metal, which further increases the heat transfer rate, compared to materials having lower coefficients of heat conduction. By supplying cryogenic refrigerant directly from the supply tube inlet connection 16, or in close proximity to the supply tube inlet connection 16, the rear portion 36 of the cryoprobe handle 12 receives cryogenic refrigerant at the coldest possible temperature to thereby cool the rear portion 36 as quickly as possible. As shown in FIG. 2, the distally located refrigerant inlet ports 43 further pass through areas of the rear portion 36 of the cryoprobe handle 12 to increase the surface area of the rear portion 36 of the cryoprobe handle 12 coming into contact with the cryogenic refrigerant.

Other embodiments of the invention are also possible. For example, where the cryogenic refrigerant from the supply tube inlet connection 16 may be passed through one or more channels disposed within or in intimate contact with the rear portion of the cryoprobe handle 36 and into the exhaust tube connection 18.

FIG. 3 is a side elevation view of a cryosurgical instrument 60 according to an alterative embodiment. The cryosurgical instrument 60 is similar to the embodiment illustrated in FIGS. 1 and 2, with the exception of a heat exchanger 62. FIG. 4 illustrates a rear view of the cryosurgical instrument 60. The heat exchanger 62 preferably comprises a tube, which is coiled over and in intimate contact with the surface of the rear portion 36 of the cryoprobe handle 12. Although a circular coil is illustrated, other configurations of the heat exchanger 62 may be embodied, as long as portions of the heat exchanger 62 contact the rear portion 36 of the cryoprobe handle 12. In the presently preferred embodiment, input cryogenic refrigerant enters the heat exchanger 62 through the supply tube inlet connection 16. The input cryogenic refrigerant enters the heat exchanger 62 from the supply tube inlet connection 16 in the direction of the arrow A17. The input cryogenic refrigerant travels through the coils of the heat exchanger 62 in a counterclockwise direction, before exiting the heat exchanger 62 at the exhaust tube connection 18 in the direction of the arrow A18. The heat exchanger 62 may vitiate any need for the rear cooling chamber 42 of the first preferred embodiment. Either or both of these cooling mechanisms, may be used, however, to achieve fast and efficient cooling off the rear portion 36 of the cryoprobe handle 12.

Although exemplary embodiments of the invention have been shown and described, many other changes, modification and substitution, in addition to those set forth in the above paragraphs, may be made by one having ordinary skill in the art without necessarily departing from the spirit and scope of this invention.

We claim:

1. A cryosurgical instrument, comprising:
   a shaft portion having an proximal open end and a distal closed end, the closed end including a freezing zone for ·freezing live tissue;
   a handle portion having a proximal end and a distal end, the handle portion proximal end including an inlet connection for receiving refrigerant and an outlet connection for exhausting refrigerant, and the handle portion distal end being connected to the proximal open end of the shaft portion;
   a cryogenic fluid supply passage having an inlet at the inlet connection and an outlet at the freezing zone, and being adapted for routing input cryogenic fluid therethrough to the freezing zone;
   a cryogenic fluid exhaust passage having an inlet at the freezing zone and an outlet at the outlet connection for exhausting cryogenic fluid from the freezing zone; and
   a heat transfer zone disposed near the inlet connection of the cryogenic fluid supply passage, the heat transfer zone including an inlet port for receiving input cryogenic refrigerant from the supply passage, a closed space wherein heat exchange can occur between input cryogenic refrigerant and surfaces defining the boundaries of said closed space, and an outlet port for exhausting only the circulating input cryogenic refrigerant to the exhaust passage.

2. The cryosurgical instrument as recited in claim 1, wherein the heat transfer zone comprises a cooling chamber.

3. The cryosurgical instrument in claim 2, wherein the inlet and outlet ports of the cooling chamber are disposed within said chamber at an optimal distance and angle for promoting the circulation of refrigerant and maximizing heat transfer between the refrigerant and the walls of said chamber.

4. The cryosurgical instrument as recited in claim 2, and further comprising an outer jacket tube, a middle tube disposed within the outer jacket tube, and an inner robe disposed within the middle tube, the inner tube comprising said fluid supply passage, the channel between the inner tube and middle tube forming said fluid exhaust passage;
   wherein the outer jacket tube, the middle tube, and the inner tube are all concentric.

5. The cryosurgical instrument in claim 4, wherein a distal end of the outer jacket tube extends distally to a distal end of the inner tube and a distal end of the inner tube extends distally of a distal end of a middle tube.

6. The cryosurgical instrument in claim 4, wherein the distal end of the outer jacket tube forms the closed end of a shaft portion and further comprises a metallic tip;

wherein the proximal open end of the outer jacket tube is connected to the distal end of a handle portion.

7. The cryosurgical instrument in claim 4, wherein a fluid tight barrier is disposed in the distal portion of the channel between the outer tube jacket and the middle tube, thereby creating a chamber at the distal closed tip that communicates with the fluid supply passage and fluid exhaust passage, but is blocked from communicating with the proximal portion of the channel between an outer jacket tube and a middle tube.

8. The cryosurgical instrument in claim 2, and further comprising an exhaust chamber in said handle portion adapted for receiving exhaust cryogenic fluid from a first proximal shaft portion of the cryogenic fluid exhaust passage.

9. The cryosurgical instrument as recited in claim 8, the exhaust chamber also being adapted for receiving refrigerant from an outlet port of the cooling chamber.

10. The cryosurgical instrument as recited in claim 7, wherein the proximal portion of the channel between the outer jacket tube and middle tube comprises an insulating channel.

11. The cryosurgical instrument in claim 1, and further comprising a cooling chamber and an exhaust chamber disposed within said handle portion; said handle portion further comprising an insulation chamber disposed within said handle portion and which surrounds portions of the exhaust chamber and cooling chamber.

12. The cryosurgical instrument as recited in claim 11, wherein the handle portion further comprises a proximal side and distal side, the proximal side of the handle portion forming a proximal side of the cooling chamber, the inner supply tube being disposed through an aperture in the proximal side of the handle portion;

wherein the insulation chamber does not surround the proximal side of the cooling chamber, and wherein the cooling chamber is adapted for cooling the proximal side of the handle portion to thereby prevent heat from transferring into the inner supply tube near the proximal side of the handle portion.

13. The cryosurgical instrument in claim 1, wherein the heat transfer zone comprises a heat exchanger coil with an inlet in communication with a cryogenic fluid supply passage and an outlet in communication with a cryogenic fluid exhaust passage.

14. The cryosurgical instrument in claim 1, wherein the heat transfer zone comprises a series of channels in the handle portion near the cryogenic fluid supply passage, an inlet in direct communication with a cryogenic fluid supply passage and an outlet in direct communication with a cryogenic fluid exhaust passage.

15. A method of cooling a handle portion of a cryosurgical instrument with an input cryogenic fluid, the handle portion having an inner supply tube passing therethrough, the handle portion being cooled in order to prevent heat transfer into the input cryogenic fluid, the method comprising the following steps:

supplying input cryogenic fluid through the inner supply tube to a freezing zone disposed near a distal end of the cryosurgical instrument;

exhausting cryogenic fluid proximally from the freezing zone;

supplying input cryogenic fluid through the inner supply tube to a heat transfer zone, the heat transfer zone being disposed at the handle portion and receiving substantially only input cryogenic fluid therein to thereby cool the handle portion; and routing both the exhaust cryogenic fluid from the freezing zone and the exhaust cryogenic fluid from the heat transfer zone out of the cryosurgical instrument.

16. The method as recited in claim 15, wherein the heat transfer zone comprises a cooling chamber.

17. The method of cooling the handle portion of a cryosurgical instrument as recited in claim 16, and further comprising a step of combining in an exhaust chamber both the exhaust cryogenic fluid from the freezing zone and the exhaust cryogenic fluid from the cooling chamber, before routing the exhaust cryogenic refrigerant from the freeze zone and the exhaust cryogenic fluid from the cooling chamber out of the cryosurgical instrument.

18. The method as recited in claim 15, wherein the heat transfer zone comprises a heat exchanger.

19. The method as recited in claim 18, wherein the heat exchanger comprises a coiled tube.

20. The method as recited in claim 18, wherein the heat exchanger comprises channels disposed within the handle portion near the inner supply tube connection.

* * * * *